US00PP18430P2

(12) United States Plant Patent
Verwer

(10) Patent No.: US PP18,430 P2
(45) Date of Patent: Jan. 15, 2008

(54) ***DAHLIA* PLANT NAMED 'KARMA RED CORONA'**

(50) Latin Name: *Dahlia hybrida*
Varietal Denomination: Karma Red Corona

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/524,393

(22) Filed: Sep. 20, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Karma Red Corona', characterized by its upright and somewhat outwardly spreading plant habit; strong and erect peduncles; freely flowering habit; decorative-type inflorescence form; large inflorescences with bright red-colored ray florets; and good garden performance and postproduction longevity.

1 Drawing Sheet

Botanical designation: *Dahlia hybrida.*
Cultivar denomination: 'Karma Red Corona'.

CROSS-REFERENCED TO RELATED APPLICATIONS

Dahlia Plant Named 'Karma Pink Corona'; Aad W.M. Verwer, applicant; filed concurrently (U.S. Plant patent application Ser. No. 11/524,394).

BACKGROUND OF THE INVENTION

The present invention relates to a new and distinct cultivar of *Dahlia* plant, botanically known as *Dahlia hybrida,* and hereinafter referred to by the name 'Karma Red Corona'.

The new *Dahlia* is a product of a planned breeding program conducted by the Inventor in Lisse, The Netherlands. The objective of the breeding program is to create new cut flower *Dahlia* cultivars that have a freely flowering habit, decorative inflorescence form, attractive ray floret coloration, and good postproduction longevity.

The new *Dahlia* is a naturally-occurring branch mutation of the *Dahlia hybrida* cultivar Karma Corona, disclosed in U.S. Plant Pat. No. 13,650. The new *Dahlia* was discovered and selected by the Inventor from within a population of plants of the cultivar Karma Corona in a controlled environment in Lisse, The Netherlands during the summer of 2001.

Asexual reproduction of the new *Dahlia* by cuttings since the spring of 2002 in a controlled environment in Lisse, The Netherlands, has shown that the unique features of this new *Dahlia* are stable and reproduced true to type in successive generations.

SUMMARY OF THE INVENTION

The cultivar Karma Red Corona has not been observed under all possible environmental conditions. The phenotype may vary somewhat with variations in environment such as temperature and light intensity, without, however, any variance in genotype.

The following traits have been repeatedly observed and are determined to be the unique characteristics of 'Karma Red Corona'. These characteristics in combination distinguish 'Karma Red Corona' as a new and distinct cultivar of *Dahlia:*

1. Upright and somewhat outwardly spreading plant habit.
2. Strong and erect peduncles.
3. Freely flowering habit.
4. Decorative-type inflorescence form.
5. Large inflorescences with bright red-colored ray florets.
6. Good garden performance and postproduction longevity.

Compared to plants of the parent, the cultivar Karma Corona, plants of the new *Dahlia* differ primarily in ray floret color as plants of the cultivar Karma Corona have golden orange-colored ray florets.

Compared to plants of the cultivar Karma Pink Corona, plants of the new *Dahlia* differ primarily in ray floret color as plants of the cultivar Karma Pink Corona have light purple-colored ray florets. In addition, plants of the new *Dahlia* are taller than plants of the cultivar Karma Pink Corona.

Plants of the new *Dahlia* can be compared to plants of the *Dahlia* cultivar Witteman's Best, not patented. In side-by-side comparisons conducted in Lisse, The Netherlands, plants of the new *Dahlia* differed from plants of the cultivar Witteman's Best in the following characteristics:

1. Plants of the new *Dahlia* were shorter than plants of the cultivar Witteman's Best.
2. Inflorescences of plants of the new *Dahlia* had longer postproduction longevity than plants of the cultivar Witteman's Best.

BRIEF DESCRIPTION OF THE PHOTOGRAPH

The accompanying colored photograph illustrates the overall appearance of the new *Dahlia.* The photograph shows the colors as true as it is reasonably possible to obtain in colored reproductions of this type. Colors in the photograph may differ slightly from the color values cited in the detailed botanical description which accurately describe the colors of the new *Dahlia*. The photograph comprises a side perspective view of typical flowering plants of 'Karma Red Corona' grown in an outdoor nursery.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photograph and description were taken.

Botanical classification: *Dahlia hybrida* cultivar Karma Red Corona.

Parentage: Naturally-occurring branch mutation of the *Dahlia hybrida* cultivar Karma Corona, disclosed in U.S. Plant Pat. No. 13,650.

Propagation:

*Type.*—By cuttings.

*Time to initiate roots, summer.*—About ten days at temperatures of about 18° C.

*Time to initiate roots, winter.*—About twelve days at temperatures of about 18° C.

*Time to produce a rooted young plant, summer.*—About 24 days at temperatures of about 18° C.

*Time to produce a rooted young plant, winter.*—About 27 days at temperatures of about 18° C. to 20° C.

*Root description.*—Fine to fleshy; tuber development has not been observed.

*Rooting habit.*—Freely branching; dense.

Plant description:

*Plant form/growth habit.*—Upright to somewhat outwardly spreading; inverted triangle plant form. Freely basal branching with about eight lateral branches and inflorescences held above the foliage on strong peduncles; bushy and dense. Moderately vigorous growth habit.

*Plant height.*—About 110 cm.

*Plant diameter or spread.*—About 40 cm.

*Lateral branches.*—Length: About 70 cm. Diameter: Towards the base, about 1.3 cm; towards the apex, about 2 mm. Internode length: About 5 cm to 17 cm. Aspect: Erect to somewhat outwardly spreading. Strength: Strong. Texture: Smooth, glabrous. Color: 144B; towards the apex, tinted with 187A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Serrate and divided; sinuses divergent.

*Length.*—Single leaves: About 5 cm. Compound leaves with three leaflets: About 14 cm. Compound leaves with five leaflets: About 21 cm.

*Width.*—Single leaves: About 3.5 cm. Compound leaves with three leaflets: About 9 cm. Compound leaves with five leaflets: About 14 cm.

*Venation pattern.*—Pinnate.

*Texture, upper and lower surfaces.*—Smooth, glabrous.

*Color.*—Developing foliage, upper surface: 146B. Developing foliage, lower surface: 147B. Fully expanded foliage, upper surface: 147A; venation, 146D. Fully expanded foliage, lower surface: 147B; venation, 146A.

*Petiole length.*—Single leaves: About 0.7 cm. Compound leaves with three leaflets: About 3 cm. Compound leaves with five leaflets: About 5 cm.

*Petiole diameter.*—Single leaves: About 3 mm. Compound leaves with three leaflets: About 3 mm. Compound leaves with five leaflets: About 3 mm.

*Petiole texture, upper and lower surfaces.*—Smooth, glabrous.

*Petiole color, upper surface.*—143C tinted with 60A.

*Petiole color, lower surface.*—Close to 160D.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 40 inflorescences develop per plant. Inflorescences persistent. Inflorescences not fragrant.

*Time to flower.*—Plants flower continuously during the summer and autumn in The Netherlands.

*Post-production longevity.*—Good postproduction longevity; inflorescences maintain good substance for about 25 days on the plant and for about one week as a cut flower.

*Inflorescence bud.*—Height: About 2.2 cm. Diameter: About 2.2 cm. Shape: Oblate to globular. Color: 151B.

*Inflorescence size.*—Diameter: About 14 cm. Depth (height): About 10 cm. Disc diameter: About 1.3 cm. Receptacle height: About 4 mm. Receptacle diameter: About 2.2 cm.

*Ray florets.*—Length: About 6.5 cm. Width: About 1.5 cm. Shape: Ovate to lanceolate. Apex: Acute. Base: Attenuate. Aspect: Initially upright to roughly perpendicular to the peduncle to reflexed; flat or recurved. Texture, upper and lower surfaces: Smooth, glabrous; satiny. Number of ray florets per inflorescence: About 108 arranged in about twelve whorls. Color: When opening, upper surface: 46A. When opening, lower surface: 21C; towards the apex, 178B; towards the base, 3A. Fully opened, upper surface: 45A with stripes of 46A; toward the base, 8A. Fully opened, lower surface: 21C; towards the apex, 178B; towards the base, 3A.

*Disc florets.*—Shape: Tubular; apex dentate. Length: About 1.3 cm. Diameter, apex: About 2 mm. Diameter, base: About 2 mm. Number of disc florets per inflorescence: About 37. Color: Immature: 7A. Mature: Apex: 21B. Mid-section: 23A. Base: Close to 1A.

*Phyllaries.*—Quantity per inflorescence: About seven arranged in a single whorl. Length: About 2.1 cm. Width: About 1.7 cm. Shape: Ovate. Apex: Acute. Base: Attenuate. Margin: Entire. Texture, upper and lower surfaces: Smooth, glabrous; satiny. Color, upper surface: 144A. Color, lower surface: 144A tinted with 187C.

*Peduncles.*—Length: Terminal peduncle: About 70 cm. Fourth peduncle: About 23 cm. Diameter: Towards the base, about 1.3 cm; towards the apex, about 4 mm. Strength: Strong. Aspect: Erect to about 10° from vertical. Texture: Smooth, glabrous. Color: 144B; towards the apex, tinted with 187A.

*Reproductive organs.*—Androecium: Quantity per disc floret: Five. Anther shape: Linear. Anther length: About 7 mm. Anther color: 16A. Pollen amount: Scarce. Pollen color: 21B. Gynoecium: Quantity per ray or disc floret: One. Pistil length: About 3 mm. Stigma shape: Lanceolate. Stigma color: Close to 12B. Style length: About 3 mm. Stigma color: 150B. Ovary color: 8A. Seeds: Length: About 1.1 cm. Diameter: About 2.1 mm. Color: 199B.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Karma Red Corona' as illustrated and described.

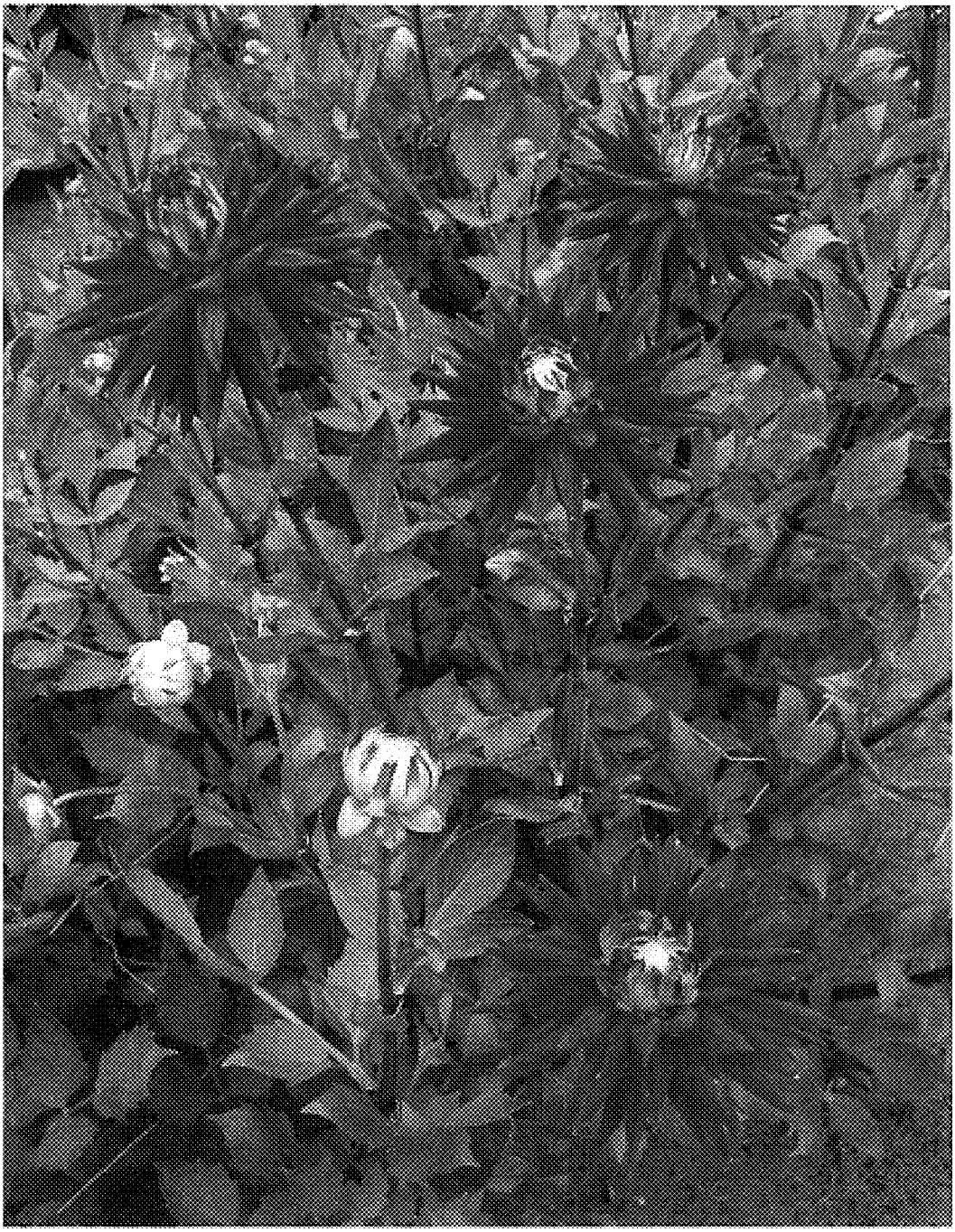

* * * * *